United States Patent [19]

Hille et al.

[11] Patent Number: 5,089,267
[45] Date of Patent: Feb. 18, 1992

[54] TRANSDERMAL THERAPEUTICAL SYSTEM COMPRISING PHYSOSTIGMINE AS ACTIVE COMPONENT AND PROCESS FOR THE PRODUCTION THEREOF

[75] Inventors: Thomas Hille; Hans-Rainer Hoffmann, both of Neuwied; Hans-Joachim Huber; Axel Koch, both of München; Gerhard Schneider, Baldham; Fritz Stanislaus, München, all of Fed. Rep. of Germany

[73] Assignees: LTS Lohmann Therapie-Systeme GmbH & Co. KG, Neuwied; Klinge Pharma GmbH, Munich, both of Fed. Rep. of Germany

[21] Appl. No.: 452,529

[22] Filed: Dec. 18, 1989

[30] Foreign Application Priority Data

Dec. 22, 1988 [DE] Fed. Rep. of Germany ....... 3843239

[51] Int. Cl.$^5$ .................... A61F 13/02; A61L 15/44; A61K 9/70; A61K 31/40
[52] U.S. Cl. ................................ 424/449; 424/448; 424/485; 424/486; 424/487; 424/196.1; 514/783; 514/879
[58] Field of Search ............... 424/449, 78, 485, 486, 424/487; 514/411, 422, 782, 788, 784, 878, 879, 912

[56] References Cited

U.S. PATENT DOCUMENTS

| | | | |
|---|---|---|---|
| 3,996,934 | 12/1976 | Zaffaroni | 424/449 |
| 4,668,506 | 5/1987 | Bawa | 424/449 |
| 4,765,985 | 8/1988 | Leeson | 424/449 |
| 4,788,063 | 11/1988 | Fisher et al. | 424/449 |
| 4,911,707 | 3/1990 | Heiber et al. | 424/449 |

OTHER PUBLICATIONS

Grant & Hackh's Chemical Dictionary, 5th Ed., pp. 146, 510.
The Merck Index, S. Budavari Ed., Merck & Co; Rahway, N.J., 1989, p. 1172.

Primary Examiner—Thurman K. Page
Assistant Examiner—Edward J. Webman
Attorney, Agent, or Firm—Sprung Horn Kramer & Woods

[57] ABSTRACT

The present invention relates to a transdermal therapeutical system for the administration of physostigmine to the skin via a cover layer which is impermeable to active substances, a pressure-sensitive adhesive reservoir layer, and optionally a removable protective layer, said reservoir layer consisting of 10–90% polymeric material selected from the groups consisting of block copolymers on the basis of styrene and 1,3-dienes, polyisobutylenes, polymers on the basis of acrylates and/or methacrylates and esters of hydrogenated colophonium, 0–30%-wt softeners on the basis of hydrocarbons and/or esters, and 0.1–20%-wt physostigmine.

14 Claims, 10 Drawing Sheets

TRANSDERMAL THERAPEUTICAL SYSTEM COMPRISING PHYSOSTIGMINE AS ACTIVE COMPONENT AND PROCESS FOR THE PRODUCTION THEREOF

The present invention relates to a transdermal therapeutical system comprising physostigmine as active component, and to a process for its production.

The application of physostigmine for the treatment of the Alzheimer disease is described in literature, whereby the efficiency of the substance has been judged differently by different authors. Since the alkaloid exhibits a high first pass effect—the bioavailability of physostigmine after oral administration is in the range of 5%—the differing results must be attributed to different forms of application.

DE-OS 35 28 979 describes a composition which in addition to physostigmine comprises a carboxylic acid of medium chain length; this composition may be applied on a bandage, an insert, or a compress, which are applied by means of a dressing. This kind of application is no therapeutical system per se; thus it is intended to provide the bandage, compress, or insert with an inner reservoir layer, an impermeable protective blocking foil, or an impermeable protective film and to apply a diffusion controlling membrane between the reservoir and the skin, which is not described in detail. Neither the diffusion controlling membrane nor the protective foils are described more precisely. The carboxylic acids are explicitly mentioned to be effective carriers for the administration of the pharmaceutical through the skin which otherwise could not penetrate through the barrier of the skin. However, this statement is not tenable from the scientific point of view.

DE-PS 36 06 892 describes a retarded application of physostigmine and other active substances, which application may be carried out transdermally. A special formulation is not disclosed. What is more, it is hinted at a pre-described formulation (U.S. Pat. No. 3,921,363).

Besides the only vague statements concerning the transdermal therapeutical systems, none of both publications deal with the instability of physostigmine which was realized very early (Eber, W., Pharmaz. Ztg. 37, 483 (1888); Herzig, J., Mayer, H., Mh. Chem 18, 379 (1897); Herzig, J., Lieb, H., ibidem 39, 285 (1918); Solvay, A. A., J. chem. Soc. (London) 101, 978 (1912); instability due to a rapid decomposition extremely limits the use of physostigmine in pharmacy).

Thus it is the object of the present invention to provide physostigmine or one of its pharmaceutically acceptable salts in the form of a transdermal therapeutical system which provides the controlled release of physostigmine or its pharmaceutically acceptable salt over a period of 24 hours and guarantees that the physostigmine does not notably decompose during the storage of the pre-fabricated transdermal therapeutical system.

According to the present invention, this object is achieved in that the physostigmine or one its pharmaceutically acceptable salts are comprised in a reservoir layer of a transdermal therapeutical system, said reservoir layer consisting of particularly selected material; whereby the components of said reservoir layer, namely polymers, resins and softeners, do neither contain free hydroxyl groups nor polyethoxy groups. Thus those components of the compound group of the esters or hydrocarbons have been selected as resin and softener components of the polymeric layer.

The stability of the active substance may further be improved by the selection of a suitable solvent or solvent mixture in the production of the transdermal therapeutical system. In this connection, solvents or solvent mixtures are used which, because of their low boiling points can be dried under mild conditions, make possible the achievement of a very low residual moisture of smaller than 0.5, preferably smaller than 0.4%.

Thus the subject matter of the present invention is a transdermal therapeutical system for the administration of physostigmine to the skin via a cover layer being impermeable to active substances, a pressure-sensitive adhesive reservoir layer, and optionally a removable protective layer, the reservoir layer of which comprises 10–90%-wt polymeric material selected from the group consisting of block copolymers of styrene and 1,3-dienes, polyisobutylenes, polymers of acrylate and/or methacrylate, and esters of hydrogenated colophonium, 0–30%-wt softeners comprising hydrocarbons and/or esters, and 0.1–20%-wt physostigmine.

In this connection, the cover layer which is impermeable to active substances may consist of flexible or inflexible material. Substances suitable for its production are polymeric foils or metal foils, such as aluminium foils which can be used alone or coated with a polymeric substrate. Textile fabrics may be used as well, if the components of the reservoir, due to their physical properties, cannot penetrate through the fabrics. According to a preferred embodiment the cover layer is a nonwoven fabric from a foil vapourized with aluminium.

The reservoir layer consists of a polymeric matrix and the active substance, whereby the polymeric matrix guarantees the coherence of the system. The matrix consists of a basic polymer and optionally of common additives. The selection of the basic polymer depends on the chemical and physical properties of the physostigmine. Examples of polymers are rubber, rubber-like synthetic homopolymers, copolymers or block polymers, polyacrylic acid esters and their copolymers. In principle all polymers are suitable which are used in the production of pressure-sensitive adhesives, which are physiologically acceptable and do not decompose physostigmine. It is particularly preferred to use those polymers consisting of block copolymers of styrene and 1,3-dienes, polyisobutylenes, or polymers of acrylate and/or methacrylate. In particular, linear styrene-isoprene block copolymers are used from the group of block copolymers of styrene and 1,3-dienes.

With regard to the matrix of the reservoir layer, acrylate-copolymers of 2-ethylhexyl acrylate, vinyl acetate, and acrylic acid with or without titanium chelate ester are preferred as acrylate polymers. Copolymers of dimethylaminoethyl methacrylates and neutral methacrylic acid esters are preferred as methacrylates. Preferred esters of hydrogenated colophonium are the methyl and glyceryl esters.

With further regard to the matrix, the kind of possible additive depends on the polymer used and the active substance: According to their function they can be divided into softeners, tackifiers, stabilizers, carriers, diffusion and penetration regulating additives or fillers. Suitable physiologically acceptable substances are known to the skilled artisan. The reservoir layer exhibits such a self-adhesiveness that a constant contact to the skin is guaranteed.

Examples for suitable softeners are diesters of dicarboxylic acids, such as di-n-butyl adipate and triglycerides, particularly medium chain triglycerides of the caprylic/capric acid of coconut oil. Further examples for suitable softeners are isopropylmyristate, dioctyl cyclohexane, etc.

The removable protective layer, which is in contact with the reservoir layer and is removed prior to application, for example, consists of the same materials as are used for the production of the covering layer, provided that they are rendered removable, for example by way of a silicone treatment. Further detachable protective layers, e.g., are polytetrafluoroethylene, treated paper, cellophane, polyvinyl chloride. If the laminate according to the present invention is cut into suitable sizes (plasters) prior to applying the protective layer, the dimensions of the protective layer to be applied may have an overlapping end, so that they may be removed from the plaster more easily.

The transdermal therapeutical system according to the present invention is produced as follows: the active substance together with the components of the pressure-sensitive adhesive reservoir layer, optionally in solution are homogeneously admixed and coated onto the cover layer which is impermeable to the active substance, then the solvent or solvents is/are removed, if necessary. Subsequently, the adhesive layer is provided with a suitable protective layer.

The invention is illustrated but not limited by the following examples:

EXAMPLE 1

20 g n-heptane and 80 g methylethyl ketone are mixed. 7.2 g physostigmine, free base, are dissolved in 90 g of said mixture. After complete dissolution of the active substance, there is added by portions 40 g of a glyceryl ester of completely hydrogenated colophonium, and 40 g of a linear styrene-isoprene-styrene block copolymer and 5.6 g triglycerides of the caprylic/capric acids of coconut oil ("medium chain triglycerides" DAB 8 (=The German Pharmacopeia, 1978). Under elimination of light it is stirred at room temperature for 8 hours up to complete dissolution, and the solution obtained is coated onto an aluminized and siliconized polyethylene foil with a 250 μm coating knife.

Figure 1:
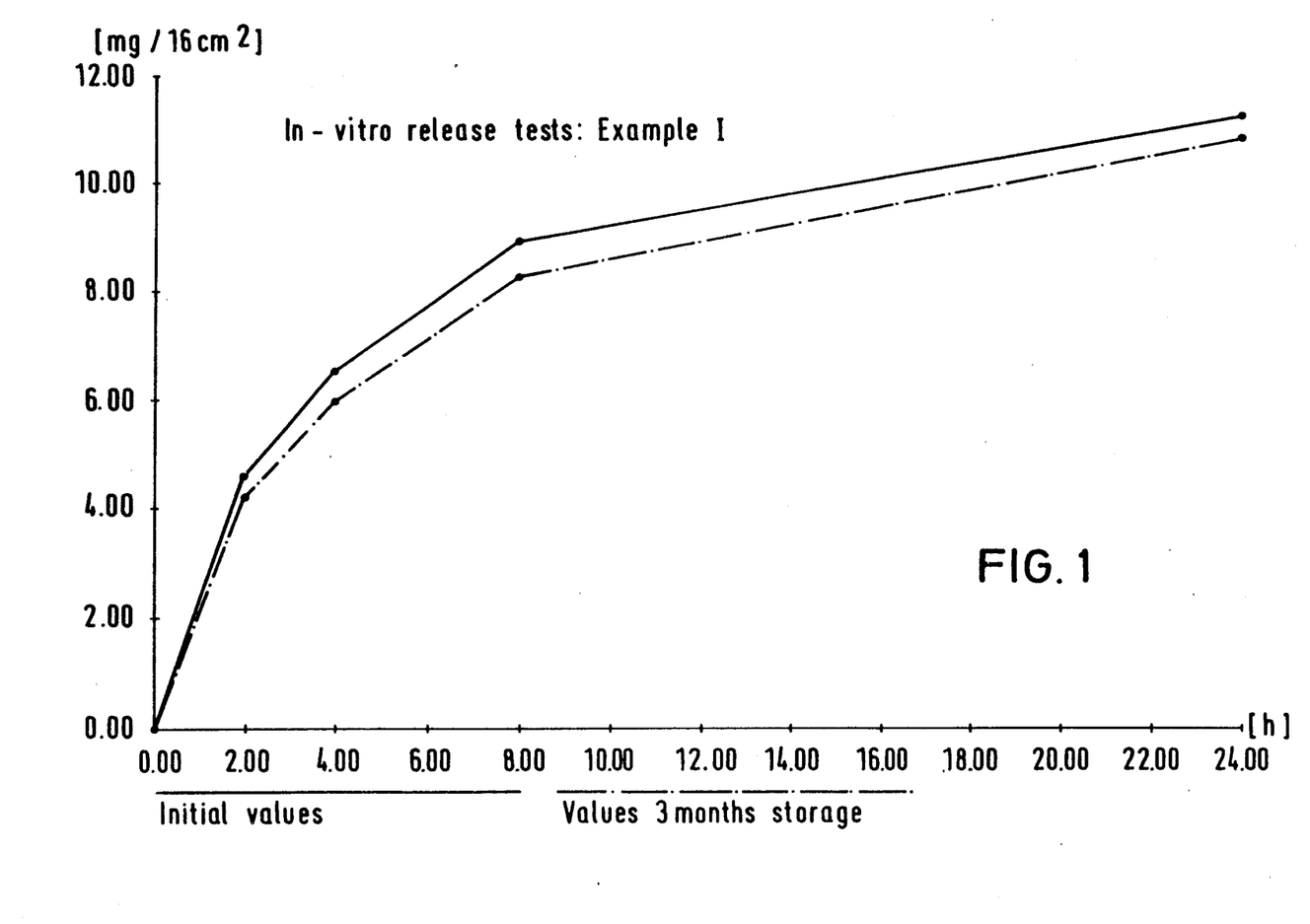
Figure 2:
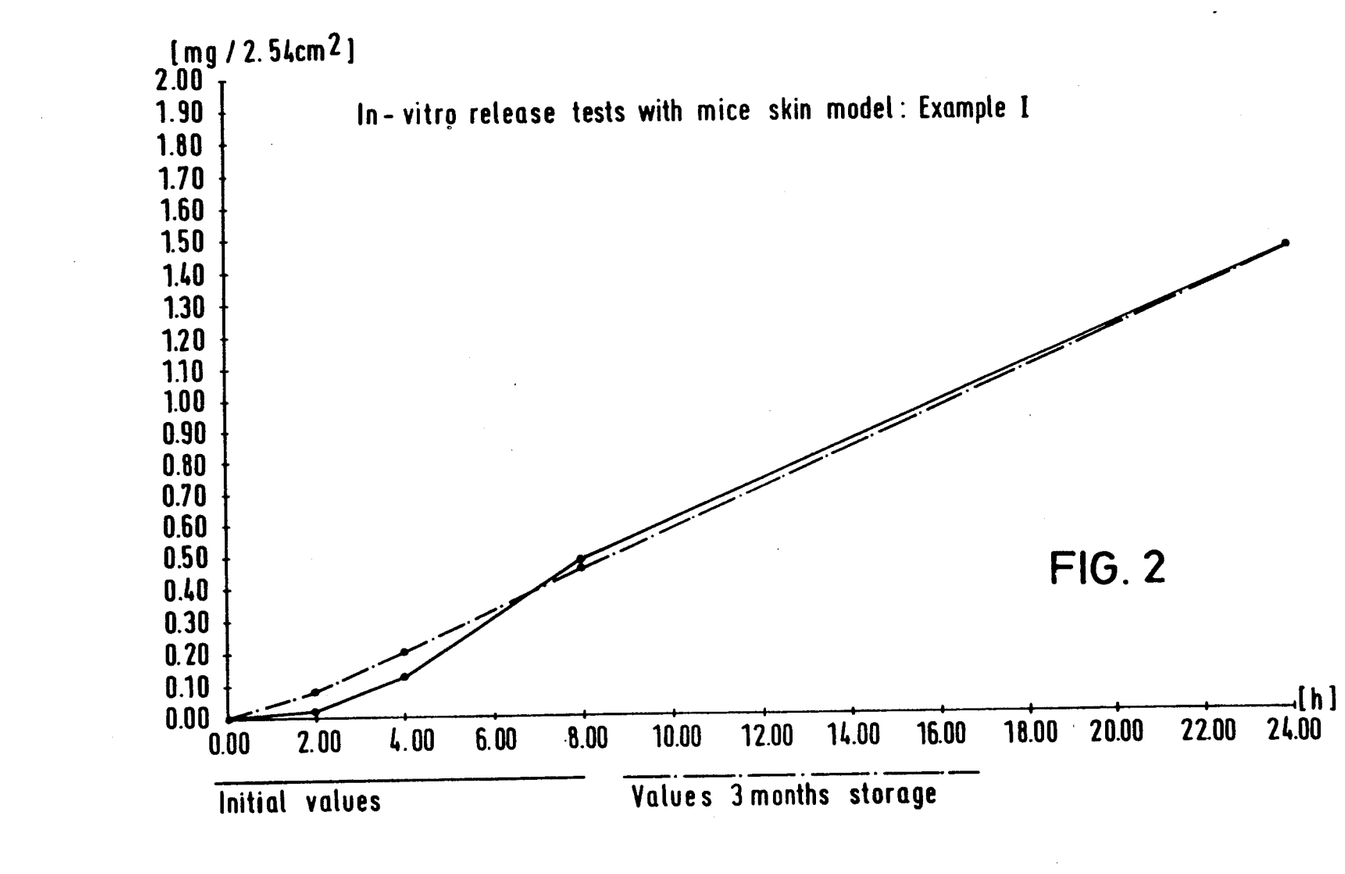

After removal of the solvent by drying at 50° C. for 25 minutes, the adhesive film is covered with a polyester foil of 15 μm. A size of 16 cm² is punched with an adequate cutting tool and the edges are separated off. The release diagrams of the preparation example 1 are shown in FIGS. 1-2. The diagrams show the controlled release of the active substance both into physiological saline and through excised rodent skin.

The curve of FIG. 1, the line of which is continuous, represents the in-vitro releases by samples which were examined immediately after their production. The discontinous curve shows releases of samples after a three-months storage at room temperature. Since both curves are nearly congruent, the above mentioned stability can be demonstrated in an impressive manner. FIG. 2 shows that the penetration rate of samples examined immediately after their production and after a three-months storage, respectively, is nearly congruent as well.

The stability of the physostigmine in the system was also shown by way of content determinations immediately after the production and after a three-months storage, respectively.

In this connection, neither eseroline and rubreserine, the decomposition products known in the literature, nor other unknown products could be detected. The following method was applied:

Preparation of the sample: 1 plaster with cover foil is divided into four parts by means of a scissors; the cover foil is removed and shaken which 50.0 ml tetrahydrofuran (of reagent purity) for at least 2 hours in a glass vessel which is capable of being closed and protected from light together with the plaster parts, then subjected to ultrasonic treatment and subsequently centrifugated. Dilution for HPLC with methanol; and further centrifugation.

Subsequently the physostigmine content in the centrifugate is determined by HPLC.

EXAMPLE 2

Figure 3:
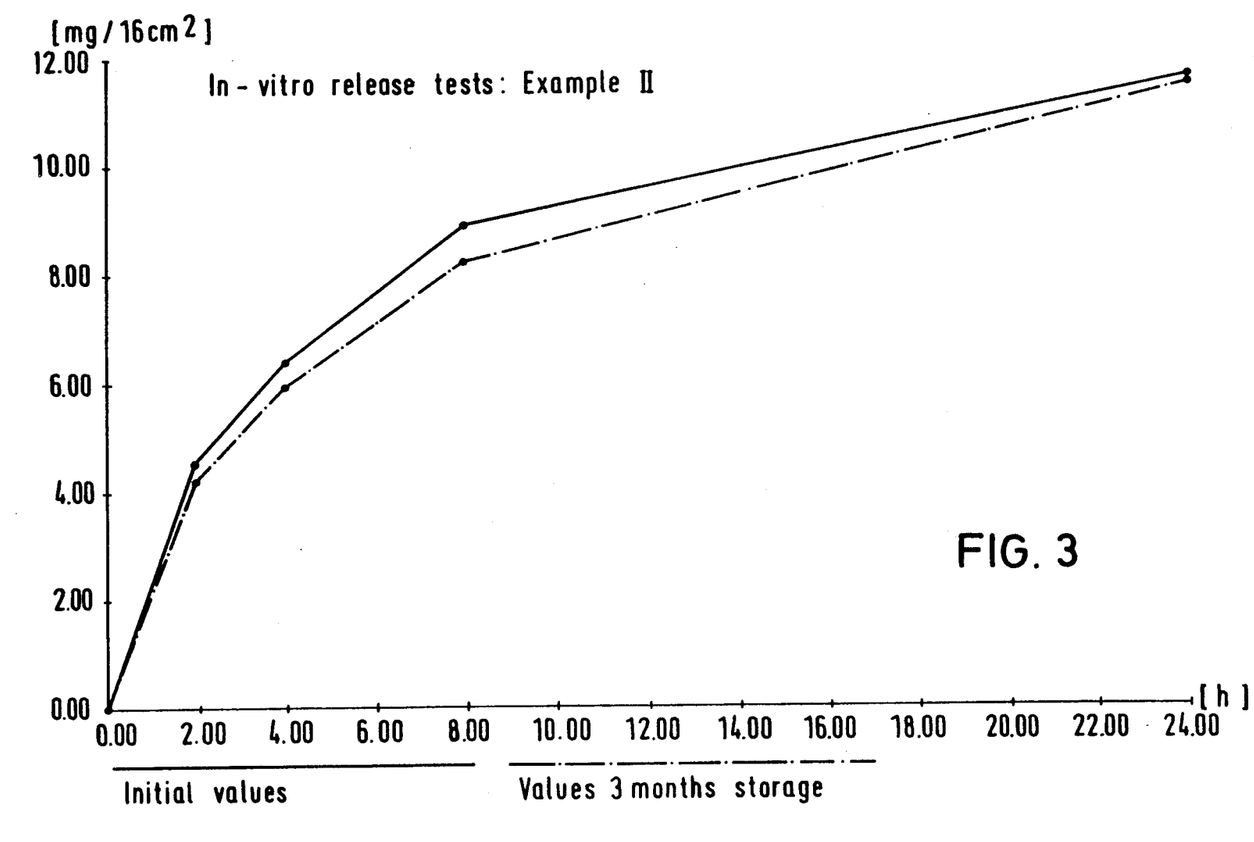
Figure 4:
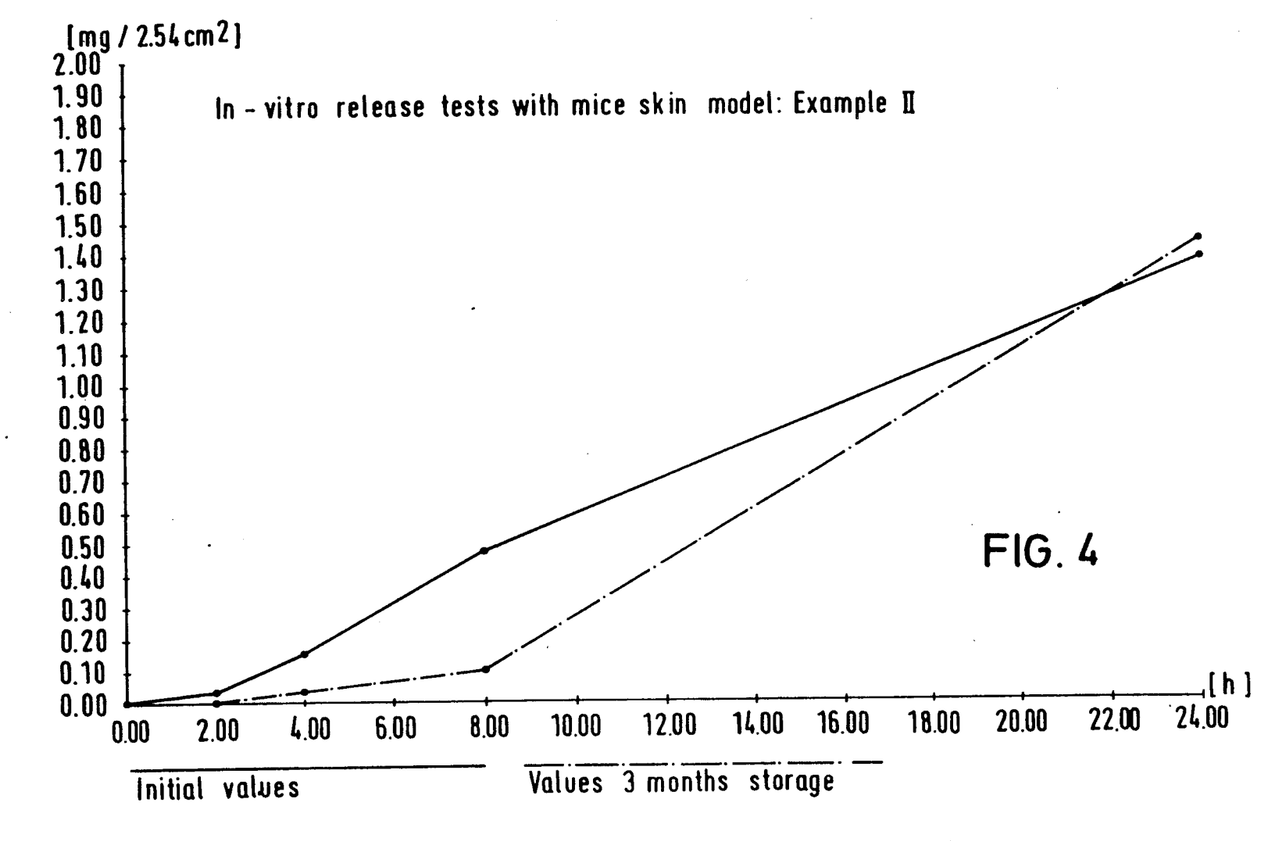

The method is carried out according to example 1, except for the fact that instead of 5.6 g triglycerides of the caprylic/capric acids 3.2 g di-n-butyl adipate are used. The release diagrams of preparation example 2 are shown in FIGS. 3-4. The diagrams show the controlled release of the active substance both into a physiological saline and through excised rodent skin.

As in example 1, the continuous line curve, represents the release of samples immediately after production. The discontinuous curve shows releases of samples which were stored for three months at room temperature. Again, the curves are nearly congruent in this case, and thus stable plasters are obtained in this example, too.

As in example 1 the physostigmine content was determined; no decomposition product could be detected after a three-months storage.

EXAMPLE 3

Figure 5:
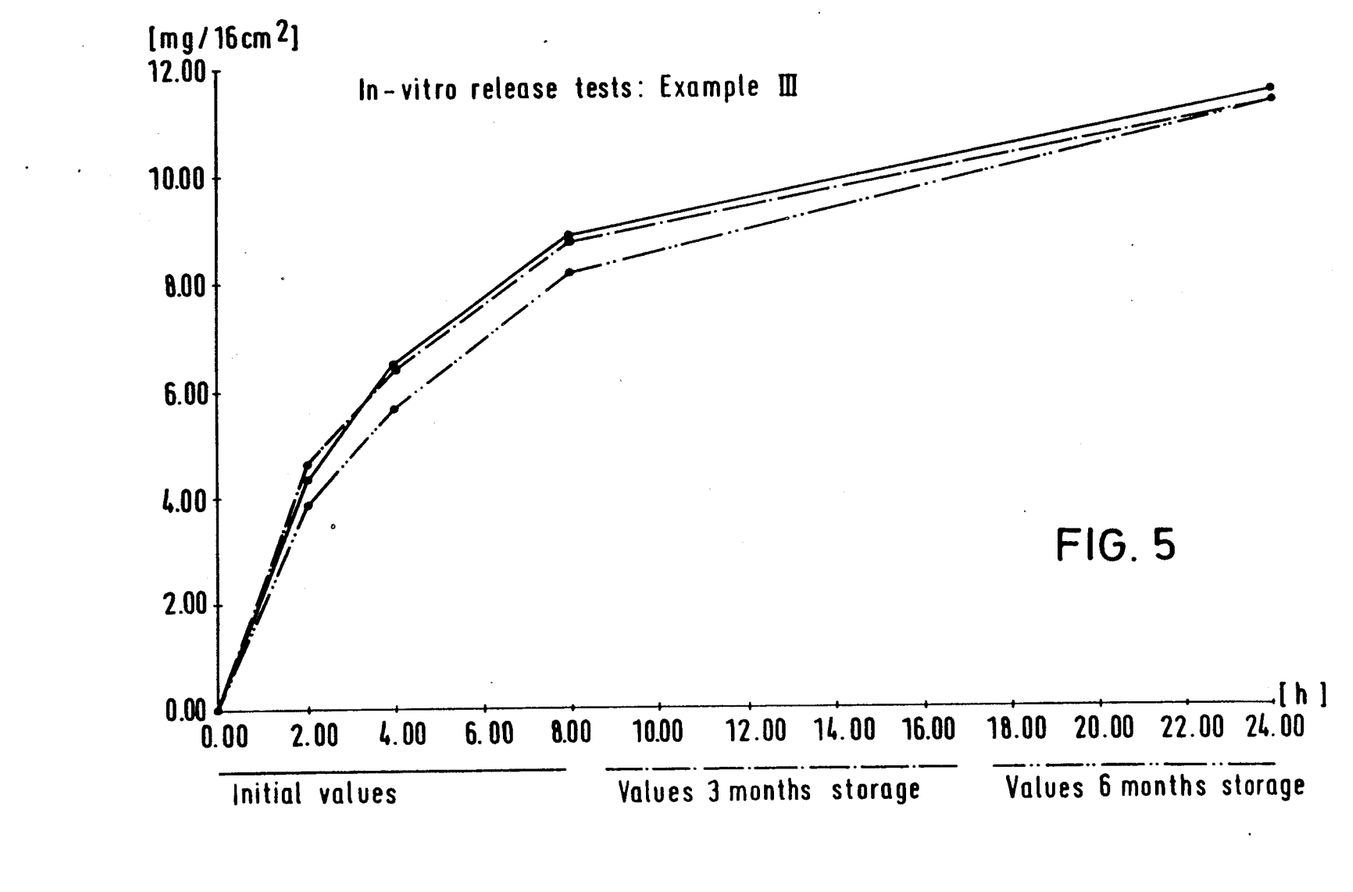
Figure 6:
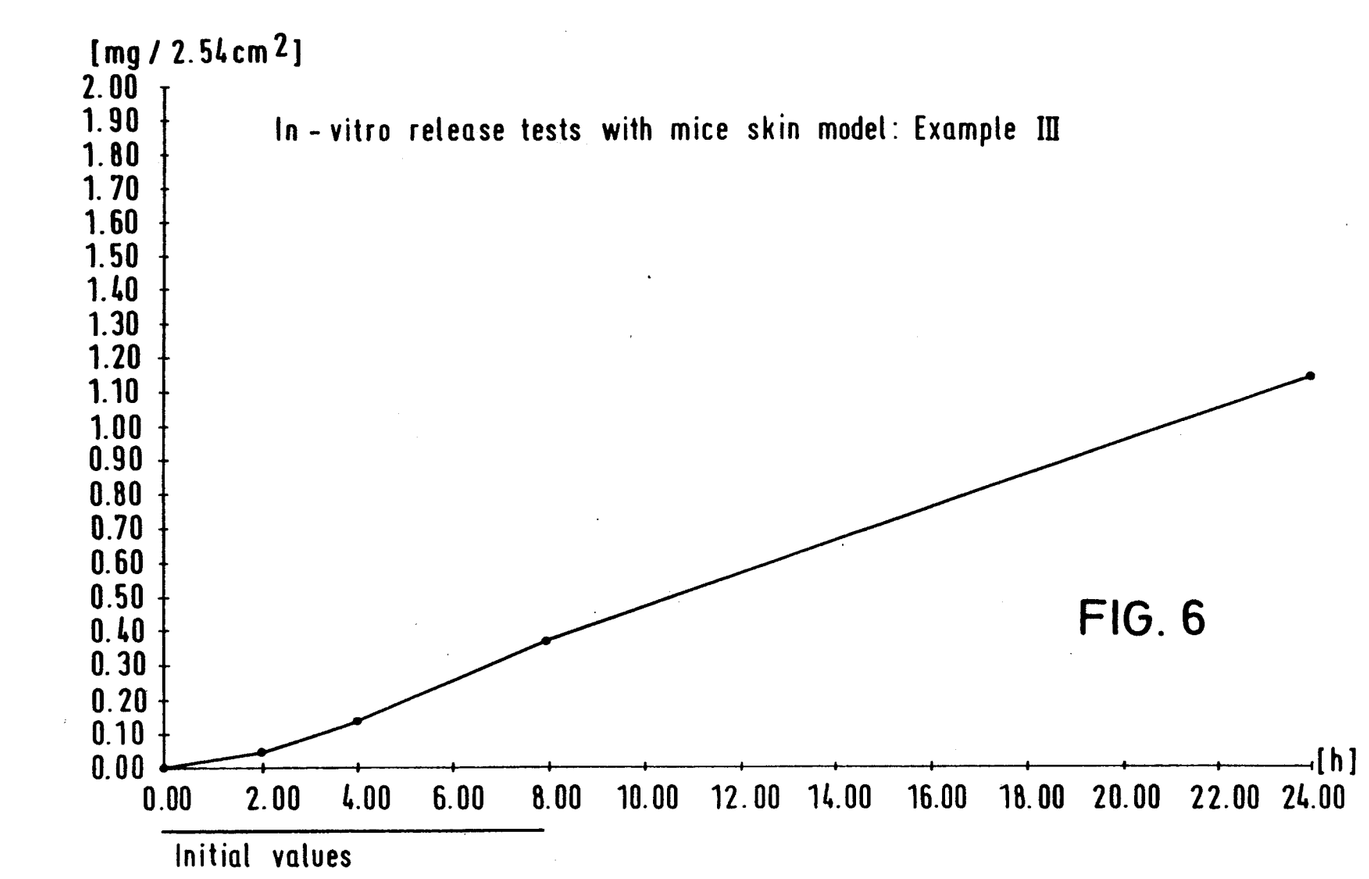

2.0 g physostigmine, free base, are weighed into a flask. 25 g of a 60% solution of glycerol colophonium ester in butanone and 25 g of a 40% solution of a styrene-butadiene block copolymer in a mixture of n-heptane and butanone at a ratio of 1:2 are added under stirring. After intense mixing, 2.5 g methylester of hydrogenated colophonium and 1.95 g triglycerides of caprylic/capric acids were added under stirring. Further performance as described in example 1. The release diagrams are shown in FIGS. 5-6. The diagrams show the controlled release of the active substance both into physiological saline and through excised rodent skin.

As in the case of examples 1 and 2, the continuous line curve shows the release of samples immediately after production. However, in contrast to the foregoing samples, the release was determined not only after a three-months storage but also after a six-months storage. Again, the three curves are nearly congruent, so that after a six-months storage the same release as immediately after production is achieved.

No decomposition product per HPLC could be detected after a six-months storage, as was the case in examples 1 and 2.

EXAMPLE 4

8.5 g physostigmine, free base, are dissolved in 21.4 g ethyl acetate together with 21.3 g of a cationic copolymer of dimethylaminoethyl methacrylate and neutral methacrylic acid esters. 8.5 g triglycerides of caprilic/capric acids and 68.3 g of a non-self-crosslinking acrylate copolymer of 2-ethylhexl acrylate, vinyl acetate and acrylic acid (50% in ethyl acetate) were added under stirring. After a maximum stirring of 30 minutes at room temperature, the adhesive mass is homogeneous. Further execution as described in example 1. The release data are given in FIGS. 7–8. The digrams show the controlled release of the active substance into physiological saline as well as through excised rodent skin.

Figure 7:
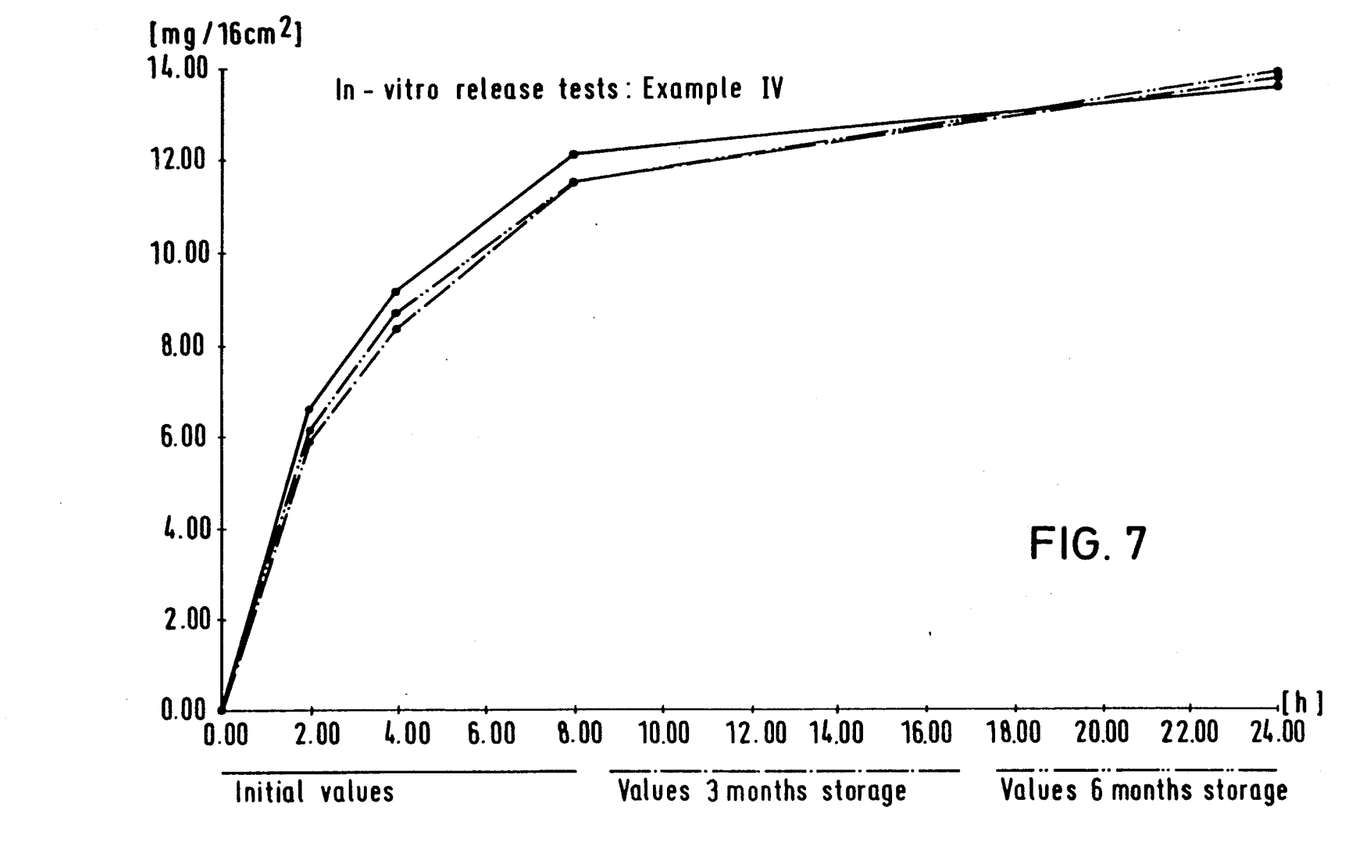
Figure 8:
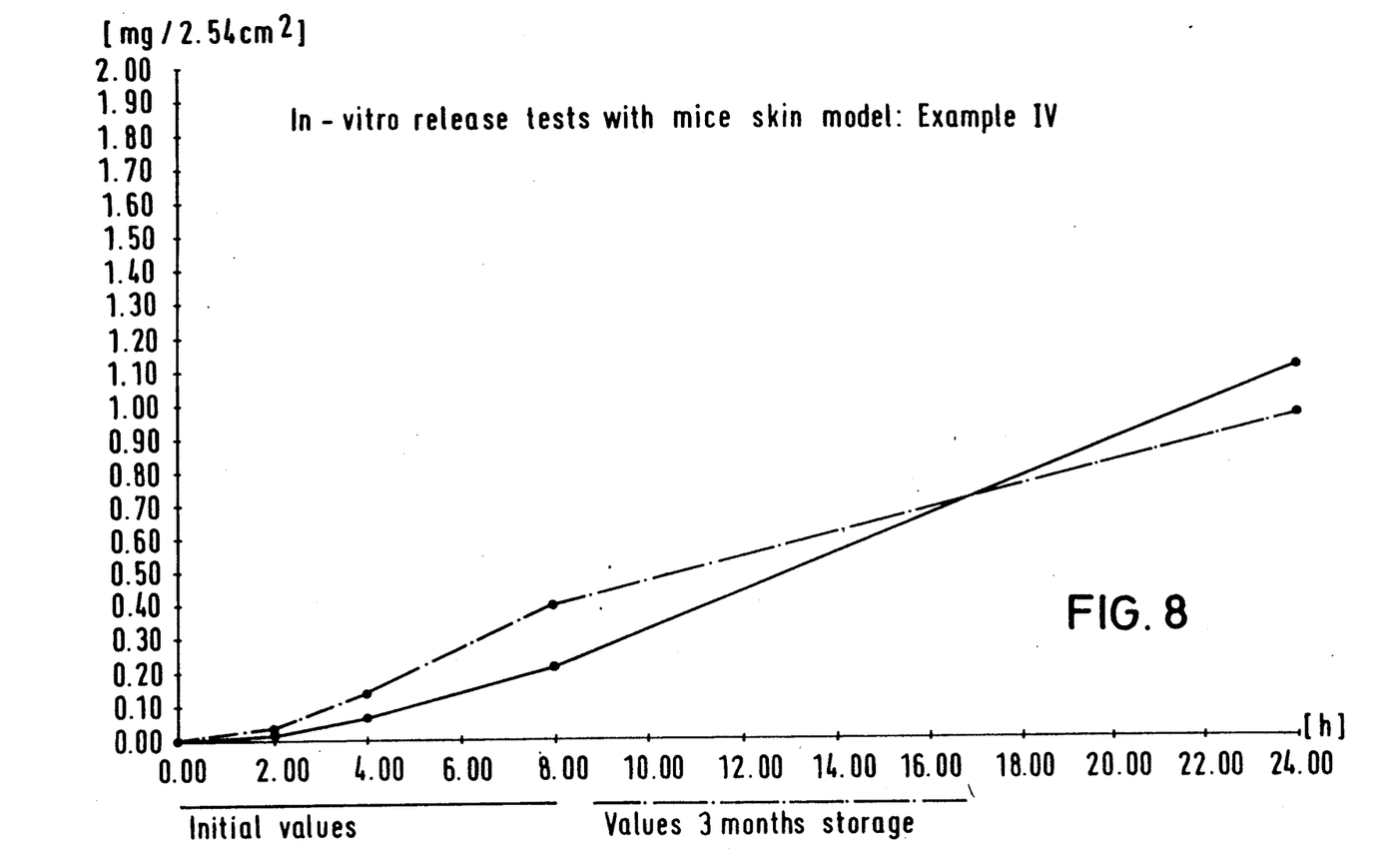

As was the case in the preceeding examples, the continuous line curve shows the release of the samples immediately after production. However, in contrast to the foregoing samples, the release was determined after a six-months storage in addition to the determination after a three-months storage. Again, the three curves are nearly congruent, so that even after a six-months storage the same release as immediately after production is achieved.

As was the case in the preceeding examples, no decomposition product could be detected by the HPLC method described under example 1 after the six-months storage.

EXAMPLE 5

Figure 9:
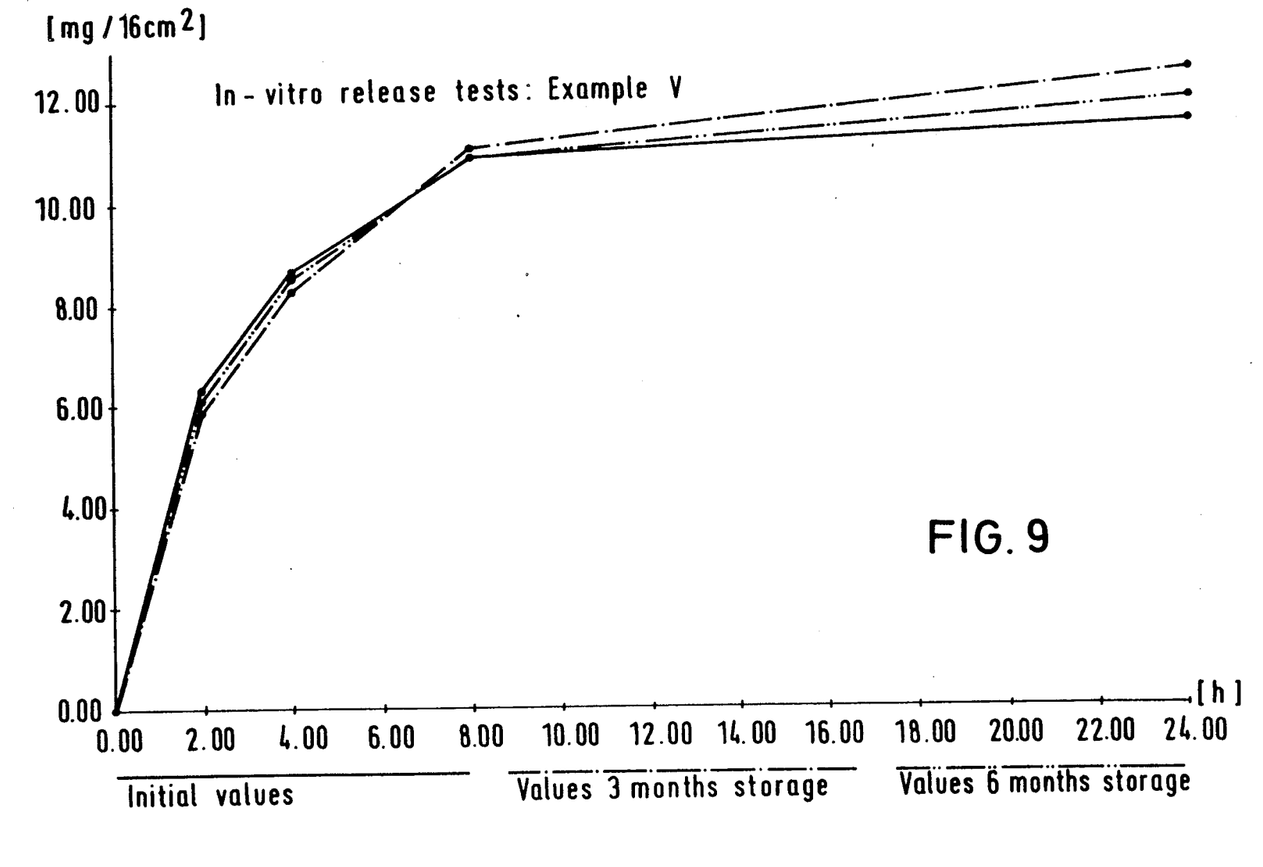
Figure 10:
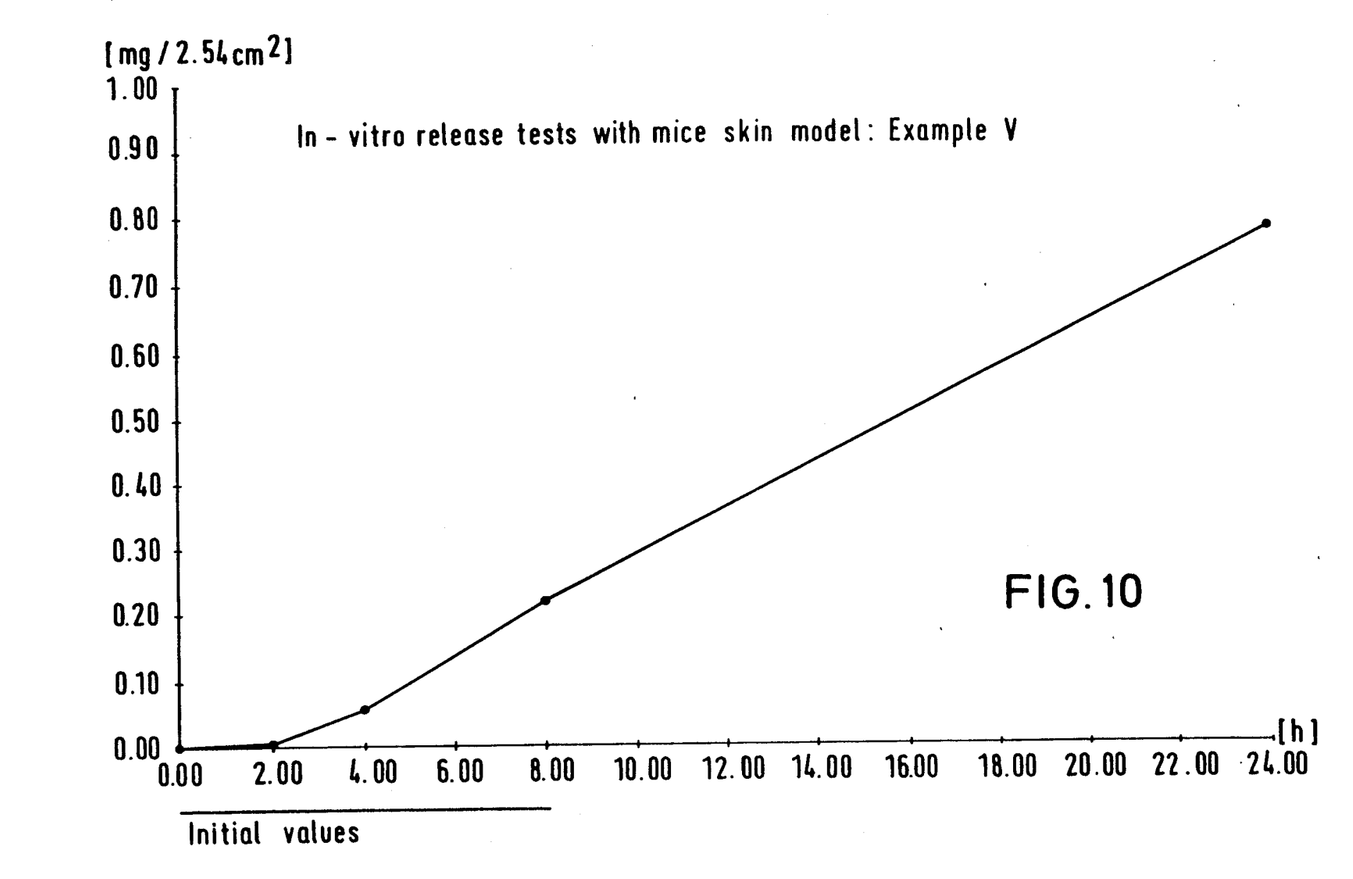

The same procedure as described in example 4 is used, with the exception that the acrylate copolymer is not dissolved 50% in ethyl acetate, but 40% in a solvent mixture (ethyl acetate:ethanol:heptane:methanol 64:25:9:2) and contains a cross-linking agent. The release diagrams are shown in FIGS. 9–10.

As was the case in the preceeding examples, the continuous line curve shows the release of the samples immediately after production. However, in contrast to the foregoing samples, the release was determined after a six-months storage in addition to the determination after a three-months storage. Again, the three curves are nearly congruent, so that after a six-months storage the same release as immediately after production is achieved.

With respect to example 5, physostigmine is subjected to a solvent—i.e. ethanol—which can hydrolytically decompose this active substance (Pfeiffer, S.; Behnsen, G. and Kühn, L., Pharmazie 27, 639 (1972), however, it is decisive that this happens only for a short period of time and under exclusion of light, since the solvent is completely removed after coating by means of gentle drying. For reasons already stated, neither the basic polymer nor the hard resin or softener attack the active substance.

It is decisive for the stability of the active substance, that the polymers, resins and softeners used do neither contain free hydroxyl groups nor polyethoxy groups, since the active substance portion, which is present in dissolved form, would be subjected to hydrolysis. For this reason, resins and softeners belonging to the compound class of the esters were chosen.

Furthermore, the selection of the solvent or solvent mixture, respectively, is decisive for the stability of the active substance, if physostigmine is subjected to the solvent prior to the drying for several hours. The portion of high-boiling solvent, possibly necessary to suppress bubble formation has to be very small. According to the present invention this is achieved in examples 1–3 in that a mixture of butanone and n-heptane forming an azeotropic mixture is chosen (ratio butanone:n-heptane 70:30; boiling point: 77° C.; boiling point of butanone: 79.6° C., boiling point of n-heptane: 98.5° C.). In doing this a maximum residual moisture of smaller than 0.4% can be achieved despite mild drying.

Since polyacrylates do not tend to form bubbles, this method was not required in examples 4 and 5.

We claim:

1. A transdermal therapeutical system for the administration of physostigmine to the skin via a cover layer which is impermeable to active substances, a pressure-sensitive adhesive reservoir layer, and optionally a removable protective layer, the reservoir layer comprising 10–90%-wt material selected from the group consisting of block copolymers of styrene and 1,3-dienes, polyisobutylenes, acrylate or methacrylate polymers and esters of hydrogenated colophonium, 0–30%-wt softeners comprising hydrocarbons or esters, and 0.1–20%-wt physostigmine.

2. The transdermal therapeutical system according to claim 1, wherein the reservoir layer material comprises linear styrene-isoprene-styrene block copolymer.

3. The transdermal therapeutical system according to claim 1, wherein the reservoir layer material comprises linear styrene-butadiene-styrene block copolymer.

4. The transdermal therapeutical system according to claim 1, wherein the reservoir layer material comprises a self-crosslinking copolymer consisting essentially of 2-ethylhexyl acrylate, vinyl acetate and acrylic acid, and titanium chelate ester as cross-linker.

5. The transdermal therapeutical system according to claim 1, wherein the reservoir layer material comprises a non-self-crosslinking acrylate copolymer consisting essentially of 2-ethylhexyl acrylate, vinyl acetate and acrylic acid.

6. The transdermal therapeutical system according to claim 1, wherein the reservoir layer material comprises as polymer a copolymer consisting essentially of dimethylaminoethyl methacrylate and a neutral methacrylic acid ester.

7. The transdermal therapeutical system according to claim 1, wherein the reservoir layer material comprises the methyl ester of hydrogenated colophonium.

8. The transdermal therapeutical system according to claim 1, wherein the reservoir layer material comprises the glycerol ester of hydrogenated colophonium.

9. The transdermal therapeutical system according to claim 1, wherein the reservoir layer comprises as softener dioctyl cyclohexane.

10. The transdermal therapeutical system according to claim 1, wherein the reservoir layer comprises as softener di-n-butyl adipate.

11. The transdermal therapeutical system according to claim 1, wherein the reservoir layer comprises as softener medium chain triglycerides.

12. The transdermal therapeutical system according to claim 1, wherein the reservoir layer comprises as softener isopropylmyristate.

13. A process for the production of a transdermal therapeutical system according to claim 1, wherein the components of the reservoir layer are dissolved in a low-boiling solvent which makes possible a drying up to a maximum residual moisture of smaller than 0.4%-wt.

14. The process for the production of a transdermal therapeutical system according to claim 13, wherein the solvent is a mixture of butanone and n-heptane.

* * * * *

UNITED STATES PATENT AND TRADEMARK OFFICE
CERTIFICATE OF CORRECTION

PATENT NO. : 5,089,267

DATED : February 18, 1992

INVENTOR(S) : Hille et al.

It is certified that error appears in the above-identified patent and that said Letters Patent is hereby corrected as shown below:

Title Page [75] Inventors: 4th inventor delete " Axel Koch " and substitute -- Axel Knoch --

Signed and Sealed this

Thirteenth Day of July, 1993

Attest:

MICHAEL K. KIRK

*Attesting Officer*   Acting Commissioner of Patents and Trademarks